(12) United States Patent
Ameye et al.

(10) Patent No.: US 7,846,478 B2
(45) Date of Patent: *Dec. 7, 2010

(54) BIOADHESIVE COMPOSITION (75) Inventors: Dieter Ameye, Waregem (BE); Jean Paul Remon, Melle (BE); Paul B. Foreman, Somerville, NJ (US); Paul H. Richardson, Vernon, NJ (US)

(73) Assignees: Henkel AG & Co. KGaA, Duesseldorf (DE); Universiteit Gent, Ghent (BE)

( * ) Notice: Subject to any disclaimer, the term of this patent is extended or adjusted under 35 U.S.C. 154(b) by 89 days.

This patent is subject to a terminal disclaimer.

(21) Appl. No.: 10/061,622

(22) Filed: Jan. 31, 2002

(65) Prior Publication Data

US 2003/0143277 A1 Jul. 31, 2003

(51) Int. Cl.
*A61K 9/14* (2006.01)
*A61K 31/74* (2006.01)
(52) U.S. Cl. .................. 424/489; 424/484; 424/78.08
(58) Field of Classification Search .............. 424/78.03, 424/78.08, 489, 488, 487, 493, 484
See application file for complete search history.

(56) References Cited

U.S. PATENT DOCUMENTS

| | | | |
|---|---|---|---|
| 4,915,948 A | 4/1990 | Gallapo et al. | |
| 5,496,861 A * | 3/1996 | Rouse et al. | 514/778 |
| 5,502,179 A * | 3/1996 | Larsen | 536/114 |
| 5,576,025 A * | 11/1996 | Akiyama et al. | 424/501 |
| 5,643,603 A | 7/1997 | Bottenberg et al. | |
| 5,895,804 A | 4/1999 | Lee et al. | |
| 5,968,500 A | 10/1999 | Robinson | |
| 6,284,235 B1 * | 9/2001 | Foreman et al. | 424/78.08 |
| 6,303,147 B1 | 10/2001 | Gilis | |

FOREIGN PATENT DOCUMENTS

| | | | |
|---|---|---|---|
| EP | 0 410 696 A1 | | 1/1991 |
| EP | 0 911 361 A1 | | 4/1999 |
| JP | 2001-121057 | * | 5/2001 |
| WO | WO 98/22097 | | 5/1998 |
| WO | WO 00/47644 | | 8/2000 |

OTHER PUBLICATIONS

Rambali et al. ("Influence of the roll compactor parameter settings and the compression pressure on the buccal bioadhesive tablet properties," in the International Journal of Pharmaceutics 220(2001), pp. 129-140).*

Burgalassi et al. ("Development and in vitro/in vivo testing of mucoadhesive buccal patches releasing benzydamine and lidocaine," in Inter International Journal of Pharmaceutics vol. 133, Issues 1-2, May 14, 1996, pp. 1-7.*

(Continued)

*Primary Examiner*—Blessing M Fubara
(74) *Attorney, Agent, or Firm*—Sun Hee Lehmann (57) ABSTRACT

The invention provides bioadhesive composition having increased bioadhesive properties, decreased irritation, and the capacity for higher drug loading. The compositions of the invention comprise intimate mixtures of a polysaccharide and a polycarboxylated polymer, and optionally also an absorption enhancer.

4 Claims, 5 Drawing Sheets

OTHER PUBLICATIONS

Borchard et al. ("The potential of mucoadhesive polymers in enhancing intestinal peptide drug absorption. III: Effects of chitosan-glutamate and carbomer on epithelial tight junctions in vitro," in J. Con. Rel., vol. 39, Issues 2-3, May 1990, pp. 131-138.*

Fuongfuchat et al. ("Rheological studies of the interaction of mucins with alginate and polyacrylate," in Carbohydrate Research, vol. 284, Issue 1, Apr. 18, 1996, pp. 85-99.*

Junginger, H.E. "Bioadhesive Polymer Systems For Peptide Delivery", Acta Pharmaceutica Technologica, DE, Wissenschaftliche Verlagsgesellschaft, Stuttgart, Sep. 1, 1990, vol. 36, No. 3, pp. 115-118.

C. Callens, E. Adriaens, K. Dierckens & J.P. Remon "Toxicological evaluation of a bioadhesive nasal powder containing a starch and carbopol 974 P on rabbit nasal mucosa and slug mucosa",www.elsevier.com/locate/jconrel, Laboratory of Pharmaceutical Technology, University of Ghent, Belgium.

Ameye et al., 2005, Polymer, 46:4338-2345.

* cited by examiner

BIOADHESIVE COMPOSITION

FIELD OF THE INVENTION

The invention relates to a bioadhesive composition, and to methods of preparing and using the bioadhesive composition.

BACKGROUND OF THE INVENTION

Bioadhesion, in particular mucoadhesion, has been of interest for the development of controlled drug delivery systems to improve buccal, nasal and oral administration of drugs. The oral and nasal cavities, for example, form convenient and easily accessible sites for drug delivery. Systemic administration via the buccal route has several advantages over peroral delivery: pre-systemic metabolism in the gastrointestinal tract and hepatic first-pass elimination are avoided (Hoogstraate and Wertz, Pharmaceutical Science and Technology Today 1(7) (1996) pp. 309-316).

Carboxylated polymers, such as poly(acrylic acid) and crosslinked poly(acrylic acid), are known to be effective as mucoadhesives (hereinafter bioadhesive compositions). Various bioadhesive compositions comprising poly(acrylic acid) are described, e.g., in WO 98/22097; EP 410,696; U.S. Pat. No. 5,643,60; U.S. Pat. No. 4,915,948; U.S. Pat. No. 5,895,804 and U.S. Pat. No. 6,284,235.

The use of bioadhesive compositions comprising carboxylated polymers has, however, been limited owing to problems associated with mucosal irritation. While attempts to reduce the degree of irritation have included blending these polymers with other materials, including polysaccharides, efforts to produce non-irritating bioadhesive matrices have resulted in compositions having decreased bioadhesion, which limits the amount of drug that can be incorporated into the composition.

There remains a need for a bioadhesive composition having increased bioadhesive properties, decreased irritation, and the capacity for higher drug loading. The current invention addresses this need.

SUMMARY OF THE INVENTION

The present invention provides a bioadhesive composition. Bioadhesive compositions of the invention have improved bioadhesive (e.g., mucoadhesive) properties resulting in increased drug loading capacity and a reduced incidence of mucosal irritation.

One aspect of the invention is directed to a bioadhesive composition comprising an intimate mixture (herein also referred to as a "comixture") of a polysaccharide and a polycarboxylated polymer. In one embodiment, the polysaccharide has a weight average molecular weight of at least about 1,000,000 Daltons and the polycarboxylated polymer has a weight average molecular weight of at least about 1,000,000 Daltons. Particularly preferred are compositions comprising a waxy starch and a crosslinked poly(acrylic acid). In one embodiment of the invention, the bioadhesive composition also comprises an aborption enhancer. The composition is prepared in such a way that each particle comprises a mixture of polysaccharide and polycarboxylated polymer. This stands in contrast to a physical mixture, which is defined herein as comprising discrete particles of polysaccharide and polycarboxylated polymer. While not wishing to assert or be bound by a particular theory, it is believed that entanglement of the polymer chains occurs at a molecular level in the intimate mixture of the invention.

Another aspect of the invention is directed to a process of preparing a bioadhesive composition comprising drying polymer solutions that may also, optionally, contain an absorption enhancer, to form a solid bioadhesive composition. Polymer solutions comprising at least one synthetic polycarboxylated polymer and at least one polysaccharide are dried to produce an intimate mixture of these components. Polymer mixtures useful in the practice of the invention will typically comprise from about 5% by weight to about 95% by weight of the polycarboxylated polymer(s) and from about 5% by weight to about 95% by weight of the polysaccharide (s). The polymers may be colloidally dispersed or dissolved in any suitable aqueous or organic solvent, including mixtures thereof. A preferred solvent is water. In a particularly preferred embodiment of the invention, the polymer solutions are co-spray dried to form an intimate mixture.

Yet another aspect of the invention is directed to a drug delivery system for the controlled delivery or administration of an active (therapeutic) agent, including but not limited to the administration of physiologically (pharmacologically) active) active agents. The drug delivery system comprises the bioadhesive composition and an active agent.

Still another aspect of the invention is directed to a method of preparing a drug delivery system comprising mixing together a bioadhesive composition and the active ingredient and applying pressure to form a tablet. Preferably, the bioadhesive composition used to prepare the drug delivery system is in the form of a powder.

A further aspect of the invention is directed to a method of administering a therapeutic agent to an individual, wherein the therapeutic agent is administered in the form of a drug delivery system comprising a bioadhesive composition and the therapeutic agent.

DETAILED DESCRIPTION OF THE INVENTION

The disclosures of all references cited herein are incorporated in their entireties by reference.

The invention provides bioadhesive compositions having increased bioadhesive capacities and decreased irritation properties. The bioadhesive compositions are prepared from a solution of a synthetic polycarboxylated polymer and a polysaccharide by co-drying the solution to form an intimate mixture of the components. The invention also provides drug delivery systems, methods of preparing drug delivery systems, and methods of administering a therapeutic agent to an individual.

Solution, as used herein, is intended to mean partial solubilization, colloidal dispersion or total solubilization.

Solid, as used herein, is intended to mean a material having less than about 10% by weight of solvent present, and includes powders. More typically, the amount of solvent present in the solid product will be less than about 5%.

The drying of the polycarboxylated polymer and a polysaccharide are conducted under conditions that result in an intimate mixture thereof as opposed to a mere physical mixture.

Physical mixture is used herein to refer to mixtures comprising discrete particles of e.g., starch and poly(acrylic acid).

Intimate mixture is used herein to refer to mixtures wherein each particle comprises a mixture of, e.g., starch and poly (acrylic acid).

By bioadhesive composition is meant a component that provides bioadhesive properties to a bioadhesive system in which it is included rather than, for instance, an excipient in a bioadhesive system.

Bioadhesive properties mean that adhesive properties are developed on contact with animal or human mucosa, skin or body tissue or vegetable or plant tissues wherein some water or an aqueous solution is present. Non-limiting examples of types of bioadhesives include intestinal, nasal, buccal, sublingual, vaginal and ocular bioadhesives.

Bioadhesion, as used herein, is intended to mean the ability of a material (synthetic or biological) to adhere to biological tissue. Bioadhesion stages can be summarized as follows. First an intimate contact must exist between the bioadhesive and the receptor tissue. Such contact results either from a good wetting of the bioadhesion surface or from the swelling of the bioadhesive. When contact is established, the penetration of the bioadhesive into the crevice of the tissue surface then takes place, or there is interpenetration of bioadhesive chains with those of the mucus, and there is formation of weak chemical bonds between entangled chains. A general description of bioadhesion may be found in Bioadhesive Drug Delivery Systems, 1999, pp. 1-10, Published by Marcel Dekker.

The bioadhesive compositions of the invention are particularly useful as sustained or controlled release preparations comprising the bioadhesive composition and an active ingredient.

The controlled release preparations of the invention find use in the administration of therapeutic agents of individuals in need of, or desirous of, the therapeutic agent. The term "individual" is used herein in its broadest sense and includes animals (both human and non-human, including companion animals such as dogs, cats and horses and livestock such as cattle and swine) and plants (both agricultural and horticultural applications being contemplated for use).

Controlled release, as used herein, is intended to mean a method and composition for making an active ingredient available to the biological system of a host. Controlled release includes the use of instantaneous release, delayed release, and sustained release. "Instantaneous release" refers to immediate release to the biosystem of the host. "Delayed release" means the active ingredient is not made available to the host until some time delay after administration. "Sustained Release" generally refers to release of active ingredient whereby the level of active ingredient available to the host is maintained at some level over a period of time. The method of effecting each type of release can be varied. For example, the active ingredient can be associated physically and/or chemically with a surfactant, a chelating agent, etc. Alternatively, the active ingredient can be masked by a coating, a laminate, etc. Regardless of the method of providing the desired release pattern, the present invention contemplates delivery of a controlled release system that utilizes one or more of the "release" methods and compositions. Moreover, the present invention can be an element of the release method and/or composition, especially with respect to sustained release systems.

The bioadhesive composition of the present invention may take up and controllably release active components such as drugs. Active components may be added using any of the known methods described in the prior art, and such addition may be carried out during and/or after the production of the bioadhesive composition. Typical active components may include, but are not limited to, a therapeutic substance or a pharmaceutically active agent such as a drug, a non-therapeutic substance such as a cosmetic substance, a local or general anesthetic or pain killer, or an opiate, a vaccine, an antigen, a microorganism, a sterilizing substance, a contraceptive composition, a protein or peptide such as insulin or calcitonin, an insecticide, a herbicide, a hormone such as a growth hormone or a seed germination hormone, a steroid, a toxin, or a marker substance.

A non-limiting list of possible active components includes hydrochlorothiazide, acetazolamide, acetylsalicyclic acid, allopurinol, alprenolol, amiloride, antiarrhythmics, antibiotics, antidiabetics, antiepileptics, anticoagulants, antimycotics, atenolol, bendroflumethiazide, benzbromarone, benzthiazide, betamethasone, bronchodilators, buphenine, bupranolol, calcitonin, chemotherapeutics, chlordiazepoxide, chlorquine, chloro thiazide, chlorpromazine, chlortalidone, clenbuterol, clomipramine, clonidine, co-dergocrine, cortisone, dexamethasone, dextropropoxyphene, diazepam, diazoxide, diclofenac, diclofenamide, digitalisglycoside, dihydralazine, dihydroergotamine, diltiazem, iron salt, ergotamine, ethacrynic acid, ethinylestradiol, ethoxzolamide, fenoterol, fludrocortisone, fluphenazine, fluorosemide, gallopamil, guanethidine, hormones, hydrochlorothiazide, hydrocortisone, hydroflumethiazide, insulin, immunosuppressives, ibuprofen, imipramine, indomethacine, coronartherapeutics, levodopa, lithium salt, magnesium salt, medroxyprogesteron acetate, manadione, methaqualone, 8-methoxypsoralen, methyldlothiazide, methyidopa, methylprednisolone, methyltestosterone, methylthiouracil, methylxanthine, metipranolol, miconazole nitrate, molsidomine, morphine, naproxen, nicergline, nifedipine, norfenefrine, oxyphenbutazone, papaverine, parmathasone, pentobarbital, perphenazine, phenobarbital, phenylbutazone, phytomenadione, pirenzepine, polythiazide, prazosine, prednisolone, prednisone, probenecid, propranolol, propylthiouracil, rescinnamine, reserpine, secbutabarbital, secobarbital, spironolactone, sulfasalazine, sulfonamide, testosterone, theophylline, thioridazine, triamcinolon, triamteren, trichloromethiazide, trifluoperazine, trifluopromazine, tuberculostatic, verapamil, virustatics, zytostatics, bromocriptine, bromopride, carbidopa, carbocromen, quinine, chlorprothixene, cimetidine, clofibrat, cyclizine, desipramine, disulfiram, domperidone, doxepine, fenbufen, flufenamine acid, flunarizine, gemfibrocil, haloperidol, ketoprofen, labetalol, lorazepam, mefenamine acid, melperone, metoclopramide, nortriptyline, noscapine, oxprenolol, oxymetholone, pentazocine, pethidine, stanozolol, sulindac, sulpiride, tiotixen.

When bioadhesive compositions of the invention are used as drug delivery vehicles, drug loads of up to about 80% are possible. A sustained release drug delivery vehicle having a high drug load may be prepared without loss of bioadhesive capacity or its sustained release profile when using the bioadhesive compositions of the invention. More typically, drugs loads of from about 0.01 to about 65% will be used in the practice of the invention.

The term "bioadhesive system" as used herein includes any system or product comprising the bioadhesive composition of this invention.

The bioadhesive composition may optionally contain one or more absorption enhancers. The absorption enhancers are incorporated in the bioadhesive composition by drying a solution of at least one solvent, at least one absorption enhancer, a synthetic polycarboxylated polymer and a polysaccharide to form a solid bioadhesive composition. Useful absorption enhancers, also referred to as permeation enhancers, include, but are not limited to, synthetic surfactants (e.g. sodium lauryl sulphate), non-ionic surfactants (e.g. laureth, polysorbate), steroidal surfactants (e.g. sodium cholate), bile salts (e.g. sodium glycocholate, sodium deoxycholate, sodium taurocholate), chelators (e.g. EDTA, disodium EDTA), fatty acids and derivatives (e.g. sodium myristate), others as sugar esters (e.g. sucrose palmitate), phosphatidylcholine, aminocaproic acid, lauramidopropylbetaine, etc. Amounts of absorption enhancers incorporated into the bioadhesive compositions of the invention will typically range from about 0.001% by weight to about 10% by weight.

Preparation of the bioadhesive compositions of this invention may be accomplished by charging solutions in at least one solvent, preferably water, of a polysaccharide and a synthetic polycarboxylated polymer into a mixing vessel and stirring until uniformly mixed. It may be necessary, as for example in the case of AMIOCA, to heat the component polymer and its solvent(s) in order to obtain solution. A partial solution, obtained for example via a batch cooker, may be used provided there is sufficient dissolution for intimate mixing with Xthe polycarboxylated polymer. In other cases it may be possible to dissolve and mix both polymers in a single step. The polycarboxylated polymer may be treated with cations to effect changes in viscosity, as would be apparent to one skilled in the art. The concentrations of the component polymer solutions are determined only by consideration of degree of solubility and a convenient viscosity for mixing and subsequent processing, as will be obvious to one skilled in the art.

The ratio of polymers in the solution mixture lies within the range of about 5 parts (on a dry weight basis) polysaccharide plus 95 parts polycarboxylated polymer to about 95 parts polysaccharide plus 5 parts polycarboxylated polymer. Preferably, the ratio lies within the range of about 25 parts polysaccharide plus 75 parts polycarboxylated polymer to about 95 parts polysaccharide plus 5 parts polycarboxylated polymer. More preferably, the ratio lies within the range of about 65 parts polysaccharide plus 35 parts polycarboxylated polymer to about 95 parts polysaccharide plus 5 parts polycarboxylated polymer.

The mixture is then dried by conventional means, including, but not limited to, spray drying, freeze drying, air drying, drum drying and extrusion, to provide a solid (e.g., a powder). The solid produced during the drying stage will preferably have a moisture content of less than about 10% by weight, preferably less than about 5% by weight. A particularly preferred method is spray drying.

The conditions used to prepare the bioadhesive compositions of the invention are sufficiently mild and/or the processing sufficiently rapid that unwanted chemical reactions, that may lead to deleterious by-products, are avoided. Thus, no purification step is needed to remove such components.

The bioadhesion compositions, e.g., prior to incorporation of an active ingredient, may be neutralized by known means, if desired.

The synthetic polycarboxylated polymers of this invention may be modified or unmodified and have a weight average molecular weight of at least 10,000 Daltons, more typically at least about 100,000 Daltons, even more typically above about 1,000,000 Daltons. Modifications may include, but are not limited to cross-linking, neutralization, hydrolysis and partial esterification.

Exemplary synthetic polycarboxylated polymers which may be used in the present invention include without limitation poly(acrylic acid), cross-linked poly(acrylic acid), poly (acrylic acid) modified by long chain alkyl acrylates, cross-linked poly(acrylic acid) modified by long chain alkyl acrylates. Typical synthetic polycarboxylated polymers of this invention include acrylic acid polymers crosslinked with allyl sucrose, allyl ethers of sucrose, allylpentaerythritol, pentaerythritol or divinyl glycol. Such polymers are available from BF Goodrich Specialty Chemicals, Cleveland, Ohio, USA under the trade names CARBOPOL®, NOVEON® and PEMULEN®. Particularly suitable are the pharmaceutical grades CARBOPOL® 971P, CARBOPOL® 934P and CARBOPOL® 974P. These examples are not limiting and the polysaccharides according to the present invention may be used in combination with virtually any synthetic polycarboxylated polymer.

The polysaccharides of the present invention are derived from natural products, including plant, animal and microbial sources. Examples of polysaccharides include starch, cellulose and gums such as galactomannans. Polysaccharide starches include maize or corn, waxy maize, potato, cassava, tapioca and wheat starch. Other starches include varieties of rice, waxy rice, pea, sago, oat, barley, rye, amaranth, sweet potato, and hybrid starches available from conventional plant breeding, e.g., hybrid high amylose starches having amylose content of 40% or more, such as high amylose corn starch. Also useful are genetically engineered starches such as high amylose potato and waxy potato starches. The polysaccharides may be modified or derivatized, such as by etherification, esterification, acid hydrolysis, dextrinization, crosslinking, pregelatinization or enzyme treatment (e.g., with alpha-amylase, beta-amylase, pullulanase, isoamylase, or glucoamylase). Particularly preferred are waxy starches. As used herein, the term "waxy" is intended to include a starch containing at least about 95% by weight amylopectin.

Preferred polysaccharides will have a weight average molecular weight of at least 10,000 Daltons, more preferably at least about 100,000 Daltons, even more preferably above about 500,000 Daltons, and most preferably greater than about 1,000,000 Daltons. While molecular weights of waxy starches are difficult to determine, waxy starches that can be used in the practice of the invention may have weight average molecular weights of 10,000,000 Daltons or more.

The invention will be described further in the following examples, which are included for purposes of illustration and are not intended, in any way, to be limiting of the scope of the invention.

EXAMPLES

Example 1

Preparation of Bioadhesive Compositions

A mixture of 10% by weight of AMIOCA waxy corn starch (obtained from National Starch & Chemical Company, Bridgewater, N.J.) and 90% water was prepared as a slurry. The mixture was heated by injecting steam at a pressure of 2.75 bar in a continuous jet cooker, maintaining the temperature at 150° C. by adjustment with jacketed cooling water.

The final starch solids content, determined by heating a small sample for 2 hours at 135° C., was 7.74%.

A 1% aqueous solution of CARBOPOL® 974P (obtained from B.F. Goodrich Company) was prepared by slowly adding the CARBOPOL to deionized water while continuously stirring until completely dispersed.

The starch and CARBOPOL solutions were uniformly mixed in such proportions as to obtain the desired ratio of starch to CARBOPOL. For example, mixing 1085 g AMIOCA solution with 5600 g CARBOPOL solution yielded a ratio of 60% AMIOCA to 40% CARBOPOL, calculated on solids basis. The solution mixture was heated in a water bath to 40° C. and spray dried using a centrifugal wheel atomizer. The inlet temperature during drying was 205° C. and the outlet temperature 110° C. The resulting product was a fine, low density, white powder comprising an intimate mixture of AMIOCA and CARBOPOL. In this example the sample is designated SD 60/40 to indicate preparation by spray drying in a ratio of 60% AMIOCA to 40% CARBOPOL. Other ratios, as used in the following examples, are similarly designated.

In the following examples, Comparative Samples, in which the starch and CARBOPOL were blended as solids to form a physical mixture are prefixed PM. The physical mixtures were prepared by dry blending AMIOCA with CARBOPOL.

Example 2

Trypsin Inhibition

One of the major barriers for successful oral peptide drug delivery is enzymatic degradation in the gastrointestinal tract. A novel approach in oral peptide drug delivery consists of the use of multifunctional polymers to inhibit proteolytic enzymes, like trypsin. Trypsin plays a key role in initiating the degradation of orally administered peptide drugs and in activating the zymogen forms of a lot of pancreatic peptidases. The trypsin inhibition capacity of SD 25/75 (prepared as described in Example 1) and a "blank" containing no polymer were determined using the trypsin inhibition assay described by Ameye et al. (J. Control. Release 68 (2000) pp. 413-417).

Amounts of 20 mmol/l N-α-benzoyl-L-arginine-ethylester (BAEE), the model substrate for trypsin, were dissolved in the polymer preparation containing 0.25% (w/v) SD 25/75 dispersed in a 50 mmol/l MES/KOH buffer, pH 6.7, with 250 mmol/l mannitol. The pH of the test medium was 6.7 and was within the optimal activity range of trypsin, which is between pH 6 and 9. At time zero 30 Enzymatic Units trypsin/ml (enzymatic activity determined according the Enzymatic Assay of Trypsin used by Sigma, Bornem, Belgium) were added to the polymer preparation, after which the solution was incubated at 37° C. for 1 hour. 50 µl of sample was withdrawn at predetermined time intervals and diluted in 1.0 ml 0.1 M HCL to stop the trypsin activity. The degradation of the substrate BAEE was studied by determining the formation of the metabolite N-α-benzoylarginine (BA) by HPLC with UV detection at 253 nm. The retention time of the metabolite peak was 1.3 min after injection of 20 µl at a flow rate of 0.75 ml/min. The degree of trypsin inhibition was expressed by the Inhibition Factor: IF=reaction rate$_{blank}$/reaction rate$_{polymer}$. The IF is defined as the ratio of the reaction rate of the metabolite concentration time curve for the enzymatic reaction carried out without polymer (Blank) and with polymer, respectively. The reaction rate was calculated by linear regression analysis of the N-α-benzoylarginine (BA) concentration versus reaction time. The correlation coefficients of the linear progress functions during 1 hour of incubation time were >0.995. The optimised HPLC method was validated. The standard curves (n=6) were linear with correlation coefficients >0.999. For repeatability (i.e. all within the same day, n=6), and for reproducibility (i.e. on different days, n=6); therefore, coefficients of variation were <3 %. The detection limit of the degradation product BA was 0.0003 mmol/l and the quantification limit 0.010 mmol/l.

Figure 1:
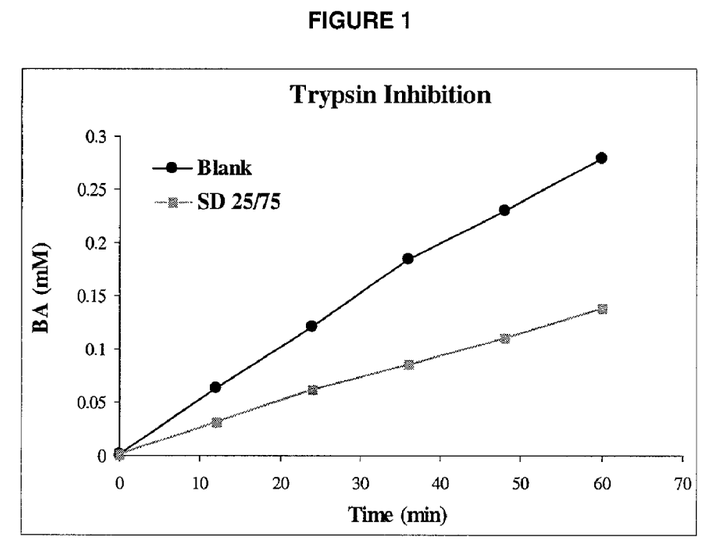
FIG. 1 is a graph showing trypsin inhibition.

Trypsin inhibition was measured as the evolution of BA in mM over a period of 60 minutes. Results are shown in Table 1 and in FIG. 1. The IF (mean±sd) of Sample SD 25/75 was calculated to be 2.05±0.05.

TABLE 1

| BA (mM) | 0 min. | 12 min. | 24 min. | 36 min. | 48 min. | 60 min. |
| --- | --- | --- | --- | --- | --- | --- |
| Blank | 0.0013 | 0.0632 | 0.1212 | 0.1837 | 0.2301 | 0.2793 |
| SD 25/75 | 0.0007 | 0.0310 | 0.0615 | 0.0855 | 0.1110 | 0.1378 |

Bioadhesive composition SD 25/75 clearly demonstrates inhibition of the enzyme trypsin compared to the blank. The high proteolytic inhibition capacity of SD 25/75 makes this composition useful for oral peptide and protein drug delivery.

Example 3

Ex Vivo Bioadhesion Measurement

To determine the bioadhesive characteristics of a material, the following method described by Bouckaert et al. (J. Pharm. Pharmacol. 45 (1993) pp. 504-507) was used.

The apparatus used for the determination of the ex vivo bioadhesion characteristics consisted of a tensile testing machine (type L1000R, Lloyd Instruments, Segenwordt, Fareham, UK), equipped with a 20 N load cell with an accuracy of less than 1%. The apparatus was connected to a computer.

Porcine gingiva were obtained from a slaughterhouse directly after slaughtering. They were rapidly frozen and stored in isotonic phosphate-buffered saline pH 7.4 (2.38 g Na$_2$HPO$_4$.2H$_2$O, 0.19 g KH$_2$PO$_4$ and 8.0 g NaCl made up to 1000 mL with demineralized water). Tablets of 100 mg of the material to be tested were directly compressed at a pressure of 1000 kg with the given polymers without any other excipient, except 1% sodium stearyl fumarate as lubricant. An eccentric compression machine (Korsch, type EKO, Frankfurt, Germany) equipped with 7 mm flat punches was used.

Figure 2:
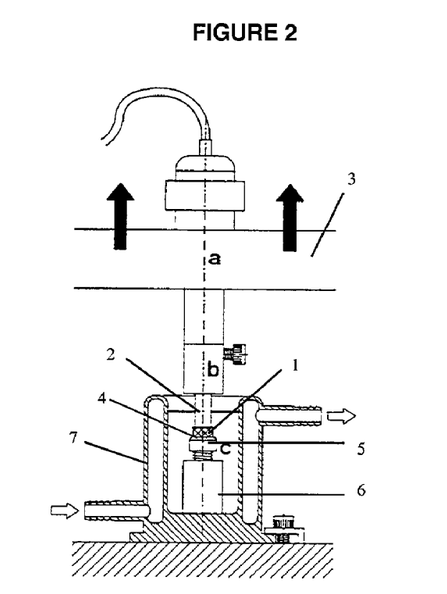
FIG. 2 is a schematic of test equipment for measuring bioadhesion.

The test equipment for measuring bioadhesion is shown schematically in FIG. 2. The tablet 1 under test was attached to the upper aluminum support 2, connected to the superior cross-sectional bar 3 of the tensile tester with a cyanoacrylate adhesive. The porcine gingival tissue (±100 mm$^2$) 4 was glued (mucosal side out) with the same adhesive to a Teflon support 5, which was connected to a PVC cylinder 6 situated at the bottom of a 150 mL thermostatically temperature-controlled beaker 7 fixed on the base of a tensile tester. Next, 15 µL of isotonic phosphate buffer (pH 7.4) was spread evenly over the mucosa 4, and the crosspiece 3 (bearing the tablet 1) was lowered at a crosshead speed of 1 mm.min$^{-1}$. After initial contact, the beaker 7 was filled with the buffer solution up to a total volume of 125 mL to act as a counterweight. The mucosa 4 and the tablet 1 were then pressed together with a force of 0.5 N for 5 min., after which the tablet 1 and the mucosa 4 were pulled apart at a constant extension rate of 5 mm.min$^{-1}$ until complete rupture of the tablet-mucosa bond was obtained.

Figure 3:
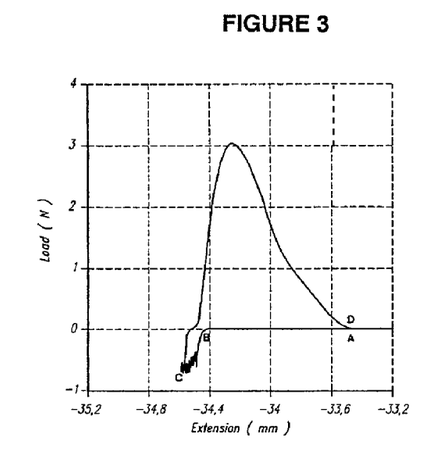
FIG. 3 is a force vs. extension diagram from which the detachment force and work of adhesion is calculated.

A force vs. extension diagram (FIG. 3) was constructed, and the maximal detachment force (N) and the work of adhesion (mJ) necessary to break the bond between tablet and mucosa were calculated. The work of adhesion is calculated from the area under the force/extension diagram.

Figure 4:
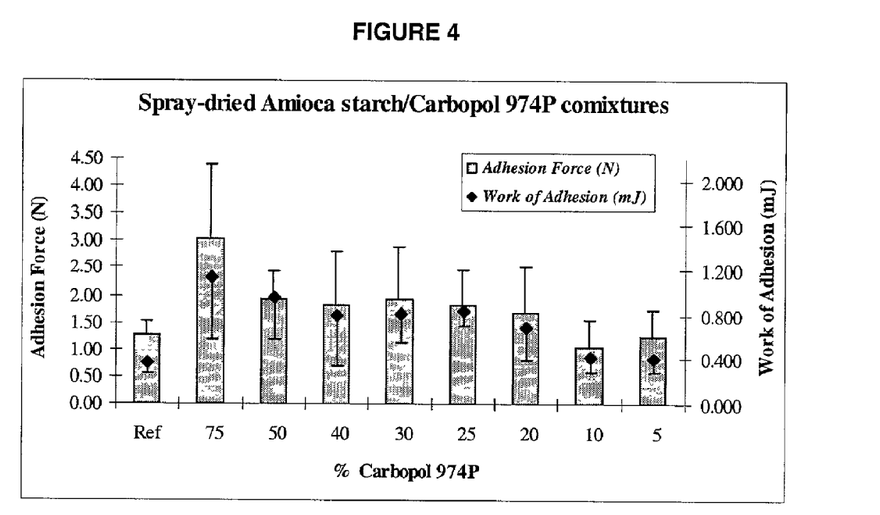
FIG. 4 shows the bioadhesive properties of the bioadhesive compositions containing different CARBOPOL® 974P concentrations.

As can be seen in FIG. 4, all AMIOCA starch/CARBOPOL® 974P comixtures showed comparable or better bioadhesive properties compared to a reference formulation, a physical mixture of 5% CARBOPOL® 974P, 94% Drum Dried Waxy Maize starch and 1% Sodium stearyl fumarate which has been shown to be effective for local (Bouckaert et al. Pharm. Res. 10 (6) (1993) pp. 853-856) as well as for systemic drug delivery (Voorspoels et al. Pharm. Res. 13 (8) (1996) pp. 1228-1232).

Figure 5:
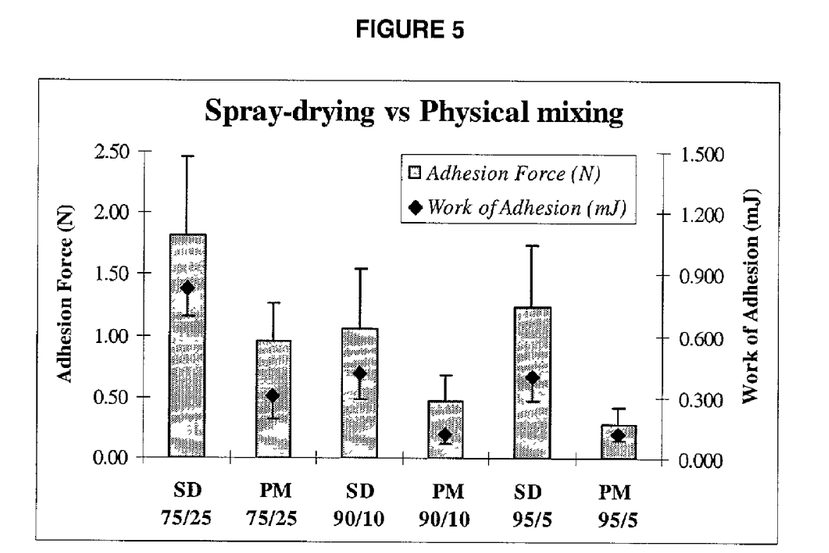
FIG. 5 compares bioadhesive properties of the comixtures of the invention to physical mixtures.

FIG. 5 clearly shows that the bioadhesive compositions prepared in accordance with this invention (SD 75/25; SD 90/10 and SD 95/5) showed improved bioadhesive capacities compared to their equivalent physical mixtures (PM 75/25; PM 90/10 and PM 95/5), respectively.

Example 4

Mucosal Irritation test on Slugs

The potential for irritation of the bioadhesive compositions of this invention was tested using a mucosal irritation test method using slugs as described in the European Patent Application (EP 0 982 589 A1, Adriaens & Remon, Ghent University).

The slugs were placed daily on 20 mg powder for a 30 min period for 5 successive days. For each powder formulation 5 slugs were used. The effect of the powders on the mucosa of the slugs was investigated by the amount of mucus produced during the contact period and by the release of proteins and enzymes after the 30 min treatment. Slugs placed in empty petri dishes were used as blanks while slugs treated with Drum Dried Waxy Maize starch/benzalkonium chloride 95/5 were used as positive control slugs.

Figure 6:
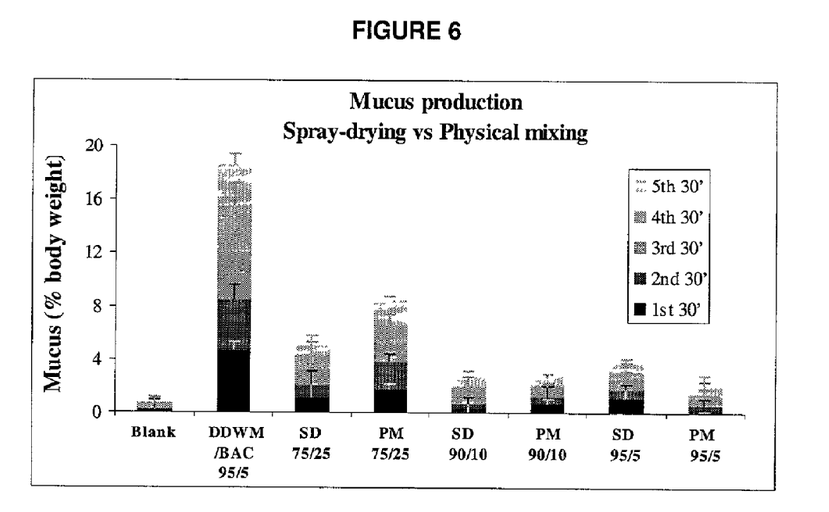
FIG. 6 illustrates the non-irritating properties of the comixtures of the invention.

As can be seen in FIG. 6, the bioadhesive composition (SD 75/25) of this invention shows a decrease in mucus production compared to the equivalent physical mixture (PM 75/25). The total mucus production of the sample SD 75/25 is below 5%, a level considered as non-irritating.

Figure 7:
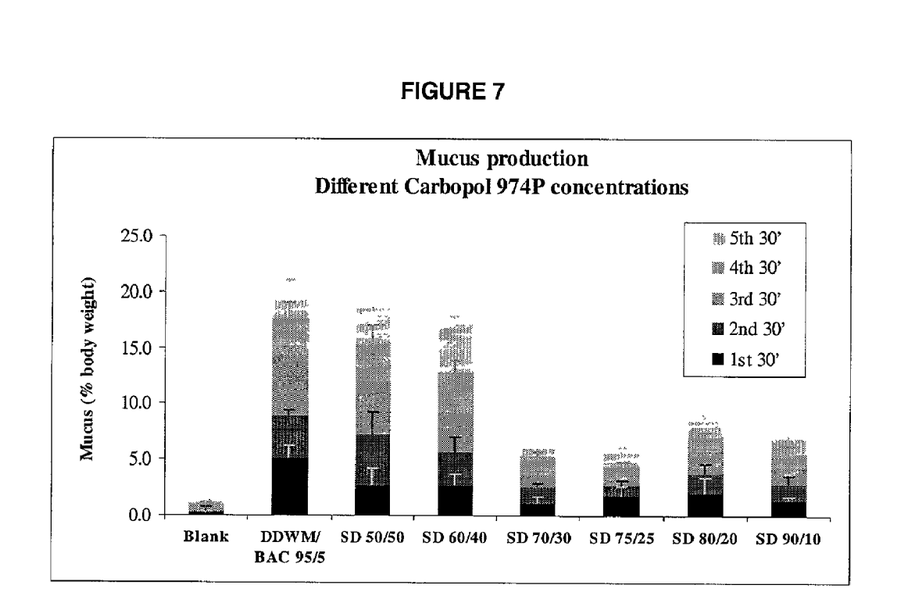
FIG. 7 shows mucus production at different CARBOPOL® concentrations.

FIG. 7 shows mucosal production of compositions containing different levels of CARBOPOL. The samples with a Carbopol® 974P level up to 30% (SD 90/10; SD 80/20; SD 75/25 and SD 70/30) are non-irritating.

Example 5

Buccal Delivery of Testosterone via a Bioadhesive Tablet 100 mg tablets containing 40 mg of Sample SD 75/25 and 60 mg of testosterone as a model drug were prepared using a compression machine. The tablets were administered to five neutered dogs. The tablets were applied in the mouth of the dogs on the buccal mucosa above the upper canine. Plasma samples were taken over 24 hours and analyzed for testosterone. The results were compared with a reference formulation, a physical mixture of 5% CARBOPOL® 974P, 94% Drum Dried Waxy Maize starch and 1% Sodium stearyl fumarate, loaded with 60 mg testosterone (Voorspoels et al. Pharm. Res. 13 (8) (1996) pp. 1228-1232). It is noted that the tablets prepared with the reference formulation were difficult to adhere, and several attempts with prolonged pressure were necessary to attach the tablets to the gingiva.

Figure 8:
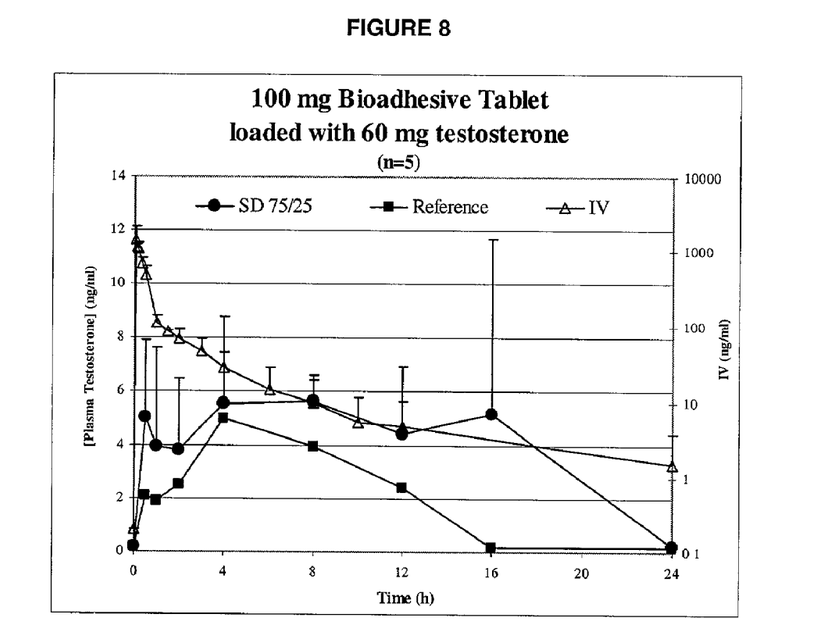
FIG. 8 shows the drug release properties of a comixture of the invention compared to a reference formulation.

FIG. 8 shows that Sample SD 75/25 provides a constant release profile over a longer period (over 16 hours) compared to the reference formulation.

Example 6

Nasal Delivery of Peptides and Proteins

After neutralization of a dispersion of SD 25/75 in distilled water, insulin was added in a ratio of 1 IU insulin per mg powder. This was lyophilized and the powder was then passed through a sieve of 63 μm mesh size. 10 mg of the powder was given to rabbits per nostril (n=8).

Figure 9:
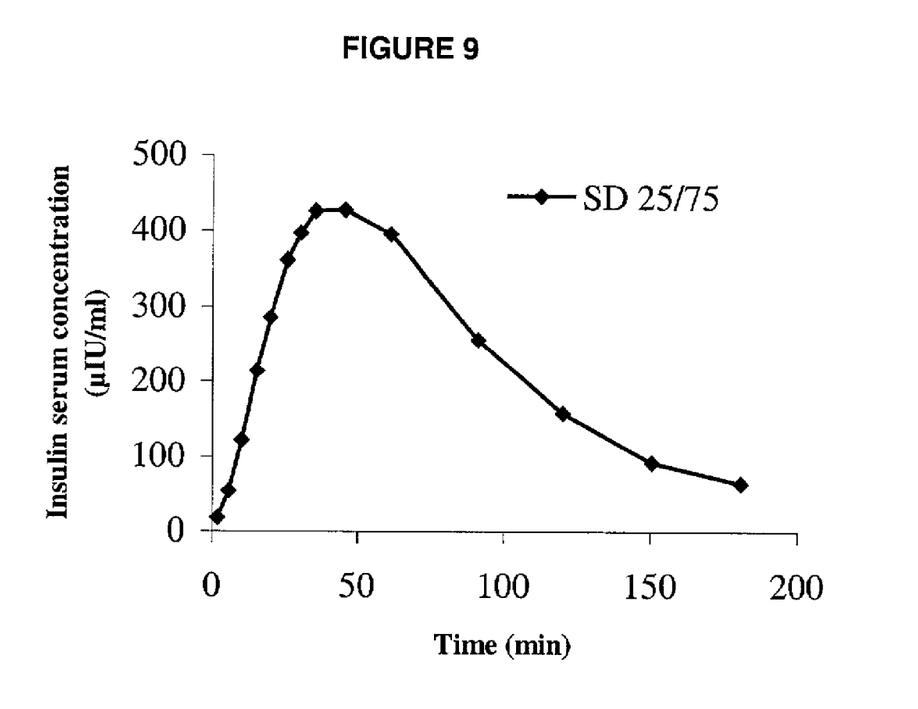
FIG. 9 shows the drug release of active ingredient from comixtures of the invention after nasal administration.

As can be seen in FIG. 9, the insulin serum concentration ($C_{max}$) was 436.0±125.9 μIU/ml and $t_{max}$ was 43.4±12.5 min. The absolute insulin bioavailability was calculated to be 17.8±4.5%. This example clearly demonstrates that peptides and proteins can be delivered via the nasal mucosa from the bioadhesive matrix compositions of the invention.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. A method of producing a bioadhesive composition comprising preparing a solution comprising at least one solvent and a polymer mixture wherein the polymer mixture comprises at least one synthetic polycarboxylated polymer component and at least one polysaccharide component and drying the solution to form a solid, said solid being a mixture of particles, wherein each particle comprises a mixture of said polysaccharide component and said polycarboxylated component; and wherein the solution is spray-dried.

2. The method of claim 1 wherein the solvent is water, the polysaccharide is a starch and the polycarboxylated polymer is cross-linked poly(acrylic acid).

3. The method of claim 1 wherein the solution further comprises an absorption enhancer.

4. A bioadhesive composition prepared by the method of claim 2.

* * * * *